United States Patent [19]

Lal

[11] Patent Number: 5,233,074
[45] Date of Patent: Aug. 3, 1993

[54] PROCESS FOR SELECTIVELY ORTHO-FLUORINATING SUBSTITUTED AROMATIC COMPOUNDS

[75] Inventor: Gauri S. Lal, Whitehall, Pa.

[73] Assignee: Air Products and Chemicals, Inc., Allentown, Pa.

[21] Appl. No.: 891,516

[22] Filed: Jun. 1, 1992

[51] Int. Cl.$^5$ ............................................. C07C 261/00
[52] U.S. Cl. ...................................... 560/30; 570/143; 570/144; 570/147; 564/182; 564/84; 564/90; 564/183; 568/28; 568/156
[58] Field of Search ..................... 570/143, 147, 144; 564/182, 183, 84, 90; 568/656, 28; 560/30

[56] References Cited

U.S. PATENT DOCUMENTS 4,828,764  5/1989  DesMarteau ...................... 260/397
5,086,178  2/1992  Banks ................................ 544/351

OTHER PUBLICATIONS

N-Fluoro-N-Alkylsulfonamides: Useful Reagents for the Fluorination of Carbanions. W. E. Barnette, J. Am. Chem. Soc., 1984, 106, 452-454.
Hudlicky, *Chemistry of Organic Fluorine Compounds*, p. 185 (1962).
Furin et al., "New Fluorinating Agents in Organic Synthesis" (1989).
R. E. Bands and G. E. Williamson, Chem. Ind. (London) 1964.
R. E. Banks et al., J. Chem. Soc., Perkin Trans., I, 1972, 1098.
R. E. Banks et al., J. Chem. Soc., Perkin Trans. I (1988) 2805.
R. E. Banks et al., J. Fluorine Chem., (1986) 34, 281.
Aldrichimica Acta, 21 (1988) 3.
S. T. Purrington et al., Chem. Rev., 86 (1986) 997.

*Primary Examiner*—Howard T. Mars
*Assistant Examiner*—Kimberly J. Kestler
*Attorney, Agent, or Firm*—Keith D. Gourley; James C. Simmons; William F. Marsh

[57] ABSTRACT

The invention describes a process for selectively preparing ortho-fluorinated substituted aromatic compounds wherein an aromatic compound containing a substituent capable of directing ortho metalation is contacted with a metalating reagent under reaction conditions sufficient to form an ortho-metalated substituted aromatic compound. The ortho-metalated substituted aromatic compound is reacted with an electrophilic fluorinating reagent under reaction conditions sufficient to form the desired ortho-fluorinated substituted aromatic compound which is then recovered from the reaction mixture. The process which utilizes a metalation intermediate prior to effecting the electrophilic fluorination step overcomes problems associated with prior art electrophilic fluorination processes which do not proceed through a regiospecifically controlled intermediate.

11 Claims, No Drawings

PROCESS FOR SELECTIVELY ORTHO-FLUORINATING SUBSTITUTED AROMATIC COMPOUNDS

TECHNICAL FIELD OF THE INVENTION

The present invention describes a novel electrophilic process for regiospecifically introducing a fluorine atom into the ortho position of a substituted aromatic compound. The fluorination process, which is effected by reacting an ortho-metalated substituted aromatic compound with an electrophilic fluorinating reagent, eliminates problems of poor selectivity and yield associated with typical prior art electrophilic fluorination processes.

BACKGROUND OF THE INVENTION

Fluorinating agents which are site-selective toward organic, especially carbanionic substrates, are especially useful in preparing pharmacologically active compounds. A number of electrophilic fluorinating agents are known but have enjoyed only limited commercial success because they are expensive, difficult to handle and sometimes provide insufficient selectivity. Nevertheless, the many advantages associated with using fluorine chemistry to regiospecifically introduce fluorine atoms into complex organic compounds and the unique properties of the fluorine-containing organic compounds obtained therefrom has led to a considerable effort to develop improved fluorination processes.

The Balz-Schiemann reaction constitutes the classical method of introducing fluorine onto an aromatic ring wherein an aromatic amine functionality situated on an aromatic ring is replaced by fluorine. A fluorine atom can be introduced into a wide range of organic compounds by diazotization of a corresponding aromatic amine in the presence of tetrafluoroboric acid. A review of the reaction as well as other methods for preparing fluoroaromatic compounds in presented in Aldrichimica Acta, 21 (1988) 3.

Known electrophilic fluorinating reagents include fluorine solutions in halogenated or other suitable solvents at low temperature (e.g., −78° C.) trifluoromethyl hypofluorite ($CF_3OF$), cesium fluoroxysulfate ($CsSO_4F$) and perchloryl fluoride ($FClO_3$). A review of these electrophilic fluorinating agents is presented in S. T. Purrington, et al, Chem Rev., 86 (1986), 997 and G. G. Furin, "New Fluorinating Agents in Organic Synthesis". Xenon difluoride ($XeF_2$) is potentially less hazardous but is too expensive to justify its use in many applications.

Attention has recently been directed to using compounds of the N-F class, i.e., having an N-F bond, as electrophilic fluorinating agents. The prototypical member of this class is perfluoro-N-fluoropiperidine (R. E. Banks and G. E. Williamson, Chem. Ind. [London], 1964 and R. E. Banks, et al., J. Chem. Soc., Perkin Trans. I, [1972], 1098). However, this compound is obtainable only in low yields by electrochemical fluorination of either pyridine (about 8% yield) or 2-fluoropyridine (about 13%) in anhydrous hydrogen fluoride. Furthermore, this reagent is inadequately active in several applications, and, on transfer of fluorine to a carbanionic substrate, may liberate imidoyl fluoride perfluoro-1-azacyclohex-1-ene which then competes with the electrophilic fluorine source for the substrate. Similar problems militate against using analogous compounds such as perfluoro-(N-fluoro-2,6-dimethylpiperidine) and perfluoro-N-fluoromorpholine, (R. E. Banks, et al., J. Chem. Soc. Perkin Trans. I [1988], 2805) and poly[perfluoro-(N-fluoropiperidin-4-ylethylnene)](R. E. Banks, et al, J. Fluorine Chem., [1986], 34 281) as electrophilic fluorinating agents.

U.S. Pat. No. 4,828,764 discloses electrophilic fluorinating agents having the structure of N-fluoro-N-perfluoroalkyl or perfluoroaryl sulfonamides represented by the formula $RfSO_2NFR$ wherein Rf represents a perfluorinated $C_1$–$C_{30}$ alkyl, $C_3$–$C_{30}$ cycloalkyl, $C_6$–$C_{14}$ aryl substituted $C_1$–$C_{10}$ alkyl or a $C_6$–$C_{14}$ aryl group and R represents a $C_1$–$C_{30}$ alkyl, $C_3$–$C_{30}$ cycloalkyl, $C_6$–$C_{14}$ aryl substituted $C_1$–$C_{10}$ alkyl, or $C_6$–$C_{14}$ aryl group optionally substituted with one or more inert substituents including fluorine. When Rf is trifluoromethyl, R may alternatively be represented by a perfluoromethyl sulfonamido group. Preferred fluorinating agents are N-fluorobis-(trifluoromethanesulfon)imide (Rf=$CF_3$ and R=$CF_3SO_2$) and N-fluoro-N-methyl-trifluoromethanesulfonamide (Rf=$CF_3$ and R=$CH_3$). The former compound (also known as the DesMarteau reagent) is a powerful electrophilic fluorinating agent which is capable of fluorinating benzene to fluorobenzene at room temperature but is tedious to prepare requiring eight or nine reactions steps from readily available material.

U.S. Pat. No. 5,086,178, assigned to Air Products and Chemicals, Inc., Allentown, Pa., discloses various electrophilic fluorinating agents of the N-F class and provides novel fluorinated diazabicycloalkane derivatives, methods for their preparation and their use as fluorinating agents. A representative derivative is 1-chloromethyl-4-fluoro-1,4-diazoniabicyclo[2,2,2]octane ditriflate.

Considerable commerical interest exists in discovering an effective electrophilic fluorination process capable of regiospecifically introducing a fluorine atom at a position ortho to a desired substituent situated on an aromatic compound wherein the reagents are stable, relatively inexpensive and readily obtainable from presently commercially available starting materials.

BRIEF SUMMARY OF THE INVENTION

The present invention relates to a process for selectively preparing ortho-fluorinated substituted aromatic compounds which comprises contacting an aromatic compound containing a substituent capable of directing ortho-metalation with a metalating reagent under reaction conditions sufficient to form an ortho-metalated substituted aromatic compound; reacting the ortho-metalated substituted aromatic compound with an electrophilic fluorinating reagent under reaction conditions sufficient to form an ortho-fluorinated substituted aromatic compound; and recovering the ortho-fluorinated substituted aromatic compound.

The claimed process overcomes problems associated with prior art electrophilic fluorination processes such as poor selectivity by utilizing a unique reaction intermediate which has not been used in prior art electrophilic fluorination processes. More particularly, while prior art electrophilic fluorination processes proceed directly to the desired fluorination product by treating a substituted aromatic compound with the desired electrophilic fluorinating agent, Applicant's process proceeds via an ortho-metalated substituted aromatic intermediate which is then subjected to the desired electrophilic fluorinating agent.

DETAILED DESCRIPTION OF THE INVENTION

The present invention describes a novel process for regiospecifically introducing a fluorine atom into the ortho position of a substituted aromatic compound. The claimed process overcomes problems associated with prior art electrophilic fluorination processes such as poor selectivity by utilizing a unique reaction intermediate which has not heretofore been used in prior art electrophilic fluorination processes. More particularly, while prior art electrophilic fluorination processes proceed directly to a desired fluorination product by treating a substituted aromatic compound with the desired electrophilic fluorinating agent, Applicant's process proceeds via an ortho-metalated substituted aromatic intermediate which is then subjected to the desired electrophilic fluorinating agent.

Applicant's process for selectively preparing ortho-fluorinated substituted aromatic compounds comprises contacting an aromatic compound containing a substituent capable of directing ortho-metalation with a metalating reagent under reaction conditions sufficient to form an ortho-metalated substituted aromatic compound; reacting the ortho-metalated substituted aromatic compound with an electrophilic fluorinating reagent under reaction conditions sufficient to form an ortho-fluorinated substituted aromatic compound; and recovering the ortho-fluorinated substituted aromatic compound.

In the initial step of the process, the aromatic compound containing a substituent group or atom capable of directing ortho-metalation is reacted with a suitable metalating reagent. A broad range of substituted aromatic compounds are capable of being fluorinated according to the present process. The sole structural requirement of the aromatic compound is that the compound contain a substituent which is capable of selectively directing metalation to a position ortho to the substituent situated on the aromatic compound when reacted with the metalating reagents presented in this Specification.

Representative substituted aromatic compounds which are capable of being regiospecifically fluorinated according to the claimed process include, but are not limited to, compounds represented by the formula Ar-R wherein Ar is an aromatic compound and R is a substituent selected from sulfonyl, 2° amides, 3° amides, ethers, sulfones, carbamates, fluorine and trifluoromethyl. Those of ordinary skill in the art can readily ascertain other suitable substituents capable of directing ortho-metalation without undue experimentation. Further information of directed metalation reactions can be obtained in an article by D. W. Slocum, et al, J. Org. Chem., 41 (1976) 3653. Typical amounts of metalating reagent with respect to the ubstituted aromatic compound generally range from 1:1 to 10:1 and preferably 1:1 to 2:1.

The above-mentioned substituted aromatic compounds are reacted with a metalating reagent such as those represented by the formula $R_n$-M wherein M is a metal selected from sodium, potassium, magnesium, lithium, cadmium or zinc and R is a 1°, 2° or 3° alkyl having from 1 to about 10 carbon atoms or a dialkylamide having alkyl group having from 1 to about 10 carbon atoms. The subscript, n, appended to the R group refers to the number of R groups required to preserve charge neutrality and will vary depending upon the particular metal. For example, when M is lithium, potassium or sodium, then n is 1 and when M is cadmium, zinc or magnesium, then n is 2. In a preferred embodiment, the metalating reagent is represented by the formula $R_n$-M wherein M is a metal selected from sodium, potassium, magnesium, lithium, cadmium or zinc; R is a 1°, 2° or 3° alkyl or dialkylamide having from 1 to about 6 carbon atoms; and n is a number required to preserve charge neutrality and which is readily deduced by those of ordinary skill in the art. One of ordinary skill in the art can also readily ascertain whether a given substituent can direct metalation to a position ortho to the substituent. The metalating reagent most commonly used for this purpose are the alkyl lithium and lithium amide type compounds (n-BuLi, sec-BuLi, tert-BuLi, lithiodiisopropylamide, etc.).

In an alternate embodiment for conducting the metalation step, a metal-metal exchange is conducted involving replacement of a lithium ion with other metallic species via reaction of the organolithium compound with various metal salts. The salts of sodium, potassium, magnesium, cadmium and zinc have been used for this purpose. Each of the metalation embodiments can be conveniently conducted under an inert atmosphere such as nitrogen or argon in a solvent which is inert to the reactants such as tetrahydrofuran (THF) or diethyl ether at a temperature ranging from $-78°$ C. to $250°$ C., preferably, the refluxing temperature of the particular solvent used. The metalation step is conducted under reaction conditions sufficient to form the desired ortho metalated substituted aromatic compound meaning that reaction conditions such as temperature and pressure are not critical to practicing the present process step and such conditions can be readily ascertained by one possessing ordinary skill in the art.

The second step of the process comprises reacting the ortho-metalated substituted aromatic compound with a suitable fluorinating reagent under reaction conditions sufficient to form the desired ortho-fluorinated substituted aromatic compound. Preferred electrophilic fluorinating reagents which have been used for this purpose are N-fluoroquinuclidinium triflate (NFQT) and N-fluoroperfluoromethyl-sulfonimide although any electrophilic fluorinating agent which is not degraded by strongly nucleophilic or basic species will react in this manner. Finally, the desired product is separated from the reaction mixture by conventional methods.

The fluorination can be carried out in any conventional manner including introducing the reagent either dissolved into a solvent or as a neat compound into a solution of the ortho-metalated aromatic compound under an inert atmosphere and stirring until the reaction is completed. The fluorination step is conducted under reaction conditions sufficient to form the desired ortho-fluorinated substituted aromatic compound meaning that reaction conditions such as temperature and pressure are not critical to practicing the present process step and such conditions can be readily ascertained by one possessing ordinary skill in the art. The flourination reaction can be carried out at temperatures ranging from $-78°$ C. to $250°$ C., and can be preferably conducted at the refluxing temperature of the particular solvent used. Typical amounts of fluorinating reagent with respect to the ortho metalated substituted aromatic compound generally range from 1:1 to 10:1 and preferably 1:1 to 2:1.

In a preferred embodiment, a complexing reagent is added to the reaction mixture prior to conducting the fluorination step. Complexing agents such as tetramethylene diamine (TMEDA) were found to considerably accelerate the fluorination step. The term, complexing agent, is well known in the art and suitable complexing agents can be readily ascertained by one of ordinary skill in the art.

The following examples are provided to further illustrate various embodiments of this invention. These examples are provided to illustrate the nature of the process described herein and are not intended to limit the scope of the claimed invention. All reagents are commercially available or can be prepared by procedures presented in the literature. Unless otherwise stated, parts and percentages in the specification and examples are given by weight.

EXAMPLE 1

PREPARATION OF 2-FLUOROANISOLE FROM N-FLUORORQUINUCLIDINIUM TRIFLATE (NFQT)

A solution of 540 mg (6.5 mmol) of anisole in 10 ml diethyl ether was added under nitrogen to a 3-necked 50 ml round bottomed flask equipped with stirring bar and $N_2$ inlet. The solution was treated with n-BuLi in hexane (0.2 ml of 2.5M solution) and the mixture was refluxed for 24 hours. This solution was added to a suspension of NFQT in diethyl ether (10 ml contained in a 3-necked round bottomed flask under nitrogen). Tetramethylene diamine (58 mg; 0.5 mmol) was added and stirred for 24 hours. The mixture was poured into 50 ml of ether, washed with 10 ml of 10% $H_2SO_4$, dried ($MgSO_4$) and evaporated in vacuo. The crude product was purified by preparative TLC (1:9 ether:hexane as eluent) to afford 36 mg (60%) of pure product. $^1$H NMR ($CDCl_3$) $\delta 3.90$ (s,3H), 6.80–7.15 (m,4H); $^{19}$F NMR ($CDCl_3$) $\delta$-136.0 (s). Mass spectrum m/z (rel. abundance) 126.05 (82% $M^+$) 127.05 (5.9%, $M^+ + 1$).

EXAMPLE 2

PREPARATION OF 2-FLUOROANISOLE FROM N-FLUORO-BISPERFLUOROMETHYL-SULFONIMIDE

A solution of 0.5 mmol 2-lithioanisole in 10 ml diethyl ether was prepared according to Example 1 from anisole and n-BuLi. A solution of N-fluorobisperfluoromethyl-sulfonimide in ether (0.5 mmol) was added dropwise under nitrogen and stirred for 24 hours at room temperature. The mixture was diluted with 50 ml ether, washed with 10 ml of 10% $H_2SO_4$, dried ($MgSO_4$) and evaporated in vacuo. Purification by preparative TLC, as recited in Example 1, gave 36 mg (60%) of 2-fluoroanisole. The spectral characterization of the product was identical to that obtained by the procedure according to Example 1.

EXAMPLE 3

PREPARATION OF N-BUTYL-2-FLUOROPHENYLKETONE

A solution of n-BuLi in hexane (0.5 mmol) was added to a solution of N,N-dimethylbenzamide in THF (75 mg. 0.5 mmol in 10 ml) in a 3-neck round bottom flask equipped with a stopper, $N_2$ inlet and septum. The mixture was stirred for one hour. Another 0.5 mmol of n-BuLi was added and stirring was continued for 16 hours at 0° C. The N-fluoroquinuclidinium triflate (125 mg, 0.5 mmol) was added followed by 150 uL (0.1 mmol) of tetramethylene diamine and the mixture was stirred for 16 hours at room temperature. The solution was diluted with ether (50 ml), washed with 10 ml of 10% $H_2SO_4$, dried ($MgSO_4$) and evaporated in vacuo. The residue was purified by preparative TLC (ether/hexane 1:9) to give 91 mg (50%) of product. $^1$H NMR ($CDCl_3$) $\delta 0.95$ (t,3H), 1.35–1.45 (m,2H), 1.65–1.75 (m,2H), 2.95 (t,2H) 7.4–7.48 (m,1H) 7.5–7.58 (m,1H), 7.90–7.95 (m,1H), 7.95–8.0 (m,1H); $^{19}$F NMR ($CDCl_3/CFCl_3$) $\delta$-189.9 (m). Mass spectrum m/z (rel. abundance) 180.05 (4.2$M^+$).

EXAMPLE 4

PREPARATION OF N-,N-DIETHYL-2-FLUOROBENZAMIDE

A solution of N,N-diethylbenzamide (885 mg, 5 mmol) in THF (10 ml) was treated with a solution of sec-BuLi (5 mmol of 1.3M) in cyclohexane and tetramethylenediamine (750 ul, 5.0 mmol) at −78° C. under $N_2$ in a 3-neck round bottom flask fitted with stopper, $N_2$ inlet and septum. The solution was stirred for 1 hour. NFQT (1.25 g, 5 mmol) was added, brought to room temperature and stirred for 16 hours. The mixture was diluted with ether (50 ml), washed with 10 ml of 10% $H_2SO_4$, dried ($MgSO_4$) and evaporated in vacuo.

The crude product was purified by preparative TLC (ether/hexane 1:9 as eluent) to afford 735 mg (75%) of pure product. $^1$H NMR ($CDCl_3$) $\delta 1.0$ (t,3H), 1.05 (t,3H), 3.20 (q,2H), 3.35 (q,2H), 7.3–7.55 (m,3H) 7.70–7.80 (m,1H); $^{19}$F NMR ($CDCl_3$) $\delta$-109.5 (s).

EXAMPLE 5

PREPARATION OF N,N-DIMETHYL-2-FLUOROBENZENESULFONAMIDE

A solution of n-BuLi in hexane (0.2 mol of 2.5M, 0.5 mmol) was added to a THF solution of N,N-dimethylbenzene sulfonamide (93 mg, 0.5 mmol in 10 ml) at 0° C. under $N_2$ in a 50 ml 3-neck round bottom flask fitted with a $N_2$ inlet, stopper and septum. After 30 minutes, tetramethylenediamine (75 ul, 0.5 mmol) was added followed by addition of NFQT (125 mg., 0.5 mmol). The mixture was stirred for 16 hours at room temperature. The solution was then poured into ether (50 mol), washed with 10 ml of 10% $H_2SO_4$, dried ($MgSO_4$) and evaporated in vacuo. Purification by preparative TLC (1:9, ether:hexane) yielded 87 mg (85%) of pure product. $^1$H NMR ($CDCl_3$) $\delta$ 2.85 (s,6H), 7.10–7.25 (m,1H), 7.30–7.40 (m,1H), 7.55–7.70 (m,1H), 7.90–8.0 (m,1H). $^{19}$F NMR ($CDCl_3$) $\delta$-60.4 (s). Mass spectrum m/z (rel. abundance) 203.05 (100% $M^+$), 204.05 (13.5 $M^+ + 1$) 205.05 (4.6, $M^+ + 2$).

EXAMPLE 6

PREPARATION OF 2-FLUORO-3-PERFLUOROMETHYLANISOLE

A solution of n-BuLi in hexanes (0.2 mol of 2.5M, 0.5 mmol) was added to a solution of trifluoromethyl anisole (0.5 mmol, 88.1 mg) in 10 ml ether contained in a 3-neck round bottom flask. Tetramethylenediamine (75 ul, 0.5 mmol) was added and the mixture was refluxed for 4 hours. This solution was added to 125 mg (0.5 mmol) of NFQT and stirred at room temperature. The mixture was diluted with 50 ml of ether, washed with 10 ml of 10% $H_2SO_4$, dried ($MgSO_4$) and evaporated in vacuo. The residue was purified by preparative TLC (1:9) ether/hexane) to afford 69 mg (71%) of pure product. $^1$H NMR (CDCl$_3$) δ 3.90 (s,3H) 7.05–7.20 (m,3H); $^{19}$F NMR (CDCl$_3$) δ-60.5 (s,3F)-136.3 (s,1F). Mass spectrum m/z (rel. abundance) 194.05 (100% M$^+$), 179.05 (38.6% M$^+$—CH$_3$).

As demonstrated by the preceding examples, Applicant's process which utilizes a metalation intermediate prior to effecting the electrophilic fluorination step overcomes problems associated with prior art electrophilic fluorination processes which do not proceed through a regiospecifically controlled intermediate.

Having thus described the present invention, what is now deemed appropriate for Letters Patent is set forth in the following claims.

I claim:

1. A process for selectively preparing ortho-fluorinated substituted aromatic compounds which comprises (a) contacting an aromatic compound containing a substituent capable of directing ortho-metalation with a metalating reagent under reaction conditions sufficient to form an ortho-metalated substituted aromatic compound; (b) reacting the ortho-metalated substituted aromatic compound with an electrophilic fluorinating reagent under reaction conditions sufficient to form a product consisting of an ortho-fluorinated substituted aromatic compound; and (c) recovering the product.

2. The process according to claim 1 wherein the reaction according to step (b) is conducted in the presence of a complexing agent and a reaction solvent which is inert with respect to the reactants.

3. The process according to claim 2 wherein the metalating reagent is represented by the formula R$_n$-M wherein M is a metal selected from sodium, potassium, magnesium, lithium, cadmium or zinc; R is a 1°, 2° or 3° alkyl having from 1 to 10 carbon atoms or a dialkylamide having alkyl group having from 1 to 10 carbon atoms; and n=1 when M is lithium, potassium or sodium and n=2 when M is cadmium, zinc or magnesium.

4. The process according to claim 3 wherein the reactions according to steps (a) and (b) are conducted at temperatures ranging from −78° C. to 250° C. in the presence of an inert atmosphere.

5. A process for selectively preparing ortho-fluorinated substituted aromatic compounds which comprises (a) contacting a substituted aromatic compound represented by the formula Ar-R wherein Ar is an aromatic compound and R is a substituent selected from sulfonyl, 2° amides, 3° amides, ethers, sulfones, carbamates, fluorine and trifluoromethyl with a metalating reagent under reaction conditions sufficient to form an ortho-metalated substituted aromatic compound; (b) reacting the ortho-metalated substituted aromatic compound with an electrophilic fluorinating reagent under reaction conditions sufficient to form a product consisting of an ortho-fluorinated substituted aromatic compound; and (c) recovering the product.

6. The process according to claim 5 wherein the reaction according to step (b) is conducted in the presence of a complexing agent.

7. The process according to claim 6 wherein the metalating reagent is represented by the formula R$_n$-M wherein M is a metal selected from sodium, potassium, magnesium, lithium, cadmium or zinc and R is a 1°, 2° or 3° alkyl or dialkylamide having from 1 to 6 carbon atoms; and n=1 when M is lithium, potassium or sodium and n=2 when M is cadmium, zinc or magnesium.

8. The process according to claim 7 wherein the reactions according to steps (a) and (b) are conducted at temperatures ranging from −78° C. to 250° C. in the presence of an inert atmosphere.

9. The process according to claim 7 wherein the reactions according to steps (a) and (b) are conducted at temperatures ranging from −78° C. to 250° C. in the presence of an inert atmosphere.

10. The process according to claim 6 wherein the metalating reagent in represented by the formula R-Li wherein R is a 1°, 2° or 3° alkyl having from 1 to 6 carbon atoms.

11. A process for selectively preparing ortho-fluorinated substituted aromatic compounds which comprises (a) contacting a substituted aromatic compound represented by the formula Ar-R wherein Ar is an aromatic compound and R is a substituent selected from sulfonyl, 2° amides, 3° amides, ethers, sulfones, carbamates, fluorine and trifluoromethyl with a metalating reagent under reaction conditions sufficient to form an ortho-metalated substituted aromatic compound; (b) reacting the ortho-metalated substituted aromatic compound with an electrophilic fluorinating reagent in the presence of a complexing agent under reaction conditions sufficient to form a product consisting of an ortho-fluorinated substituted aromatic compound; and (c) recovering the product.

* * * * *